United States Patent

Sjøholm et al.

[11] Patent Number: 5,912,150
[45] Date of Patent: Jun. 15, 1999

[54] PYRODICTIUM XYLANASE, AMYLASE AND PULLULANASE

[75] Inventors: Carsten Sjøholm, Allerød, Denmark; Garabed Antranikian, Seevetal, Germany

[73] Assignee: Novo Nordisk A/S, Bagsvaerd, Denmark

[21] Appl. No.: 08/855,429

[22] Filed: May 13, 1997

Related U.S. Application Data

[62] Division of application No. 08/737,559, filed as application No. PCT/DK95/00211, May 31, 1995, Pat. No. 5,688,668.

[30] Foreign Application Priority Data

Jun. 15, 1994 [DK] Denmark ................................ 0682/94

[51] Int. Cl.$^6$ .............................. C12P 19/14; C12P 19/44; C12N 9/28; C12N 1/00
[52] U.S. Cl. ............................ 435/99; 435/71.1; 435/74; 435/202; 435/822
[58] Field of Search ............................ 435/99, 202, 822, 435/74, 71.1

[56] References Cited

U.S. PATENT DOCUMENTS

| | | | |
|---|---|---|---|
| 4,966,850 | 10/1990 | Yu et al. ................................ | 435/200 |
| 5,370,997 | 12/1994 | Antranikian et al. .................... | 435/712 |
| 5,491,086 | 2/1996 | Gelfand et al. ......................... | 435/194 |

FOREIGN PATENT DOCUMENTS

WO 93/08275  4/1993  WIPO .
WO 93/19171  9/1993  WIPO .

OTHER PUBLICATIONS

Yoshioka et al., "Production and Characterization of Thermostable Xylanase From Talaromyces Byssochlamydoides", Agric. Biol. Chem. 45(3), 1981 pp. 579–586.

Brown et al., "Characterization of Amylolytic Enzyme Activities Associated With Hyperthermophilic Archaebacterium *Pyrococcus Furiosus*", Applied and Enviromental Microbiology, Jul. 1990, vol. 56, No. 7, pp. 1985–1991.

Koch et al., "Purification and Properties of a Hyperthermoactive α– Amylase From The Archaeobaterium *Pyrococcus Woesei*", Arch Microbiol (1991) 11: pp. 572–578.

*Primary Examiner*—Robert A. Wax
*Assistant Examiner*—Elizabeth Slobodyansky
*Attorney, Agent, or Firm*—Steve T. Zelson; Valeta Gregg

[57] ABSTRACT

The present invention relates to an amylase from the genus Pyrodictium, specifically to an amylase from *Pyrodictium abyssi* and more specifically to an amylase from *Pyrodictium abyssi*, DSM 6158, which has amylase activity optimum at temperatures in the range 110–120° C., determined at pH 5.5 with starch as a substrate.

5 Claims, 2 Drawing Sheets

PYRODICTIUM XYLANASE, AMYLASE AND PULLULANASE

CROSS-REFERENCE TO RELATED APPLICATIONS

This application is a divisional application of application Ser. No. 08/737,559, filed Nov. 13, 1996 now U.S. Pat. No. 5,688,668, which is a 371 of PCT/DK95/00211, filed May 31, 1995, and claims priority of Danish application Serial No. 0682/94 filed Jun. 15, 1994, the contents of which are fully incorporated herein by reference in their entirety.

FIELD OF INVENTION

The present invention relates to a novel thermostable amylase and to a novel thermostable pullulanase and their use in the production of sweeteners and ethanol from starch, and to a novel thermostable xylanase and its use in the paper and pulp industry.

BACKGROUND OF THE INVENTION

The production of sweeteners from starch has been largely improved by application of different microbial enzymes to obtain better quality and yields, but the necessity of performing several steps of the starch-hydrolysing process at elevated temperatures means that there is still a need for new starch-hydrolysing enzymes with increased thermal stability.

It is known that Pyrococcus, e.g. *Pyrococcus woesei* and *Pyrococcus furiosus*, for reference see *Arch. Microbiol.* 155, 1991, pp. 572–578, and *Appl. Env. Microbiol.* 56, 1990, pp.1985–1991, can produce highly thermostable amylases.

The paper and pulp industry is using xylanase compositions in the bleaching process to enhance the brightness of bleached pulps, to decrease the amount of bleaching chemicals, e.g. chlorine, used in the bleaching stages, and to increase the freeness of pulps in the recycled paper process.

Thermostable xylanases from Thermotoga have been described, for reference see *Biochem. J.* 277(2), 1991, pp. 413–418.

It is the object of this invention to provide a xylanase, an amylase and a pullulanase with temperature optimum at 100° C. or above 100° C.

SUMMARY OF THE INVENTION

We have unexpectedly found that a novel thermostable xylanase, a novel thermostable amylase and a novel thermostable pullulanase can be obtained from the genus Pyrodictium, a genus not previously reported to produce thermostable xylanases, amylases and pullulanases; these new enzymes have temperature optimum around 110–120° C.

Accordingly, the invention provides a xylanase preparation, characterized by being producible by cultivation of a xylanase producing strain of the genus Pyrodictium, and an amylase preparation, characterized by being producible by cultivation of an amylase producing strain of the genus Pyrodictium, and a pullulanase preparation, characterized by being producible by cultivation of a pullulanase producing strain of the genus Pyrodictium.

BRIEF DESCRIPTION OF DRAWINGS

The present invention is further illustrated by reference to the accompanying drawings, in which.

DETAILED DISCLOSURE OF THE INVENTION

The Microorganism

Figure 1:
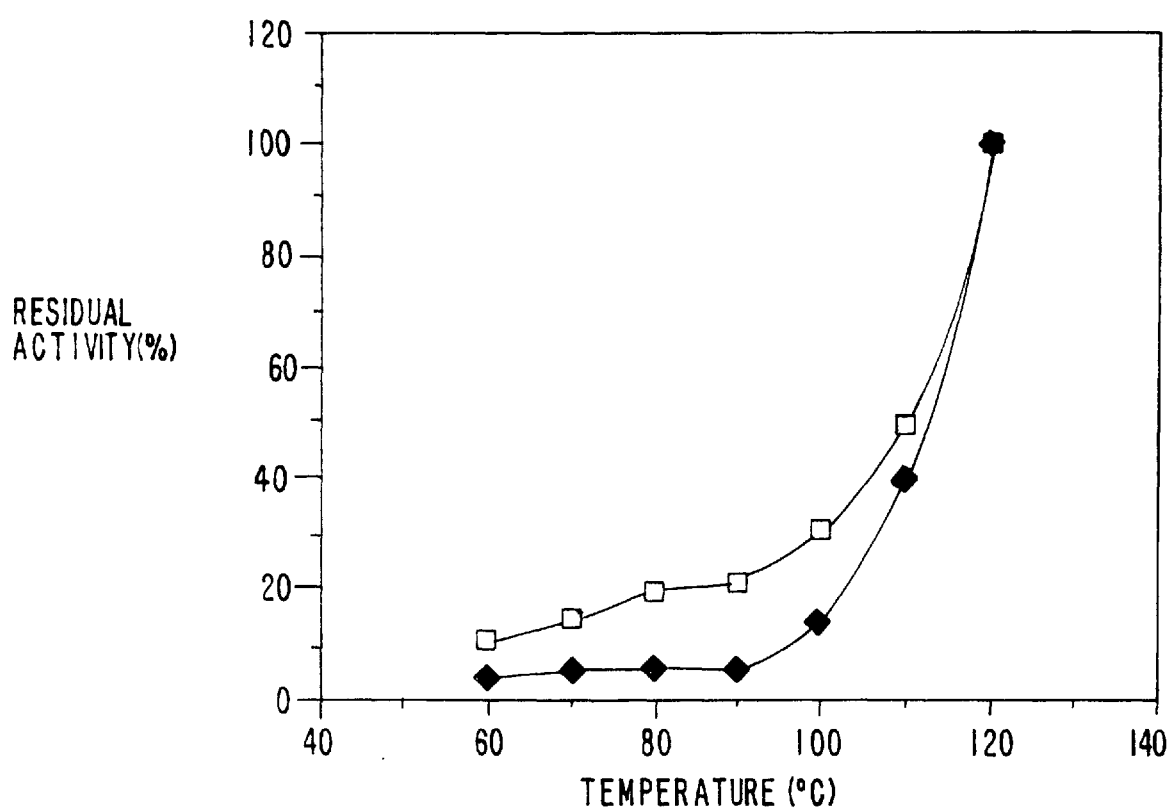
FIG. 1 shows the relative activity (% rel.) of an amylase (♦) and a pullulanase (□) of the invention at various temperatures (determined at pH 5.5 with starch and pullulan, respectively, as substrate).

Looking for extremely thermostable enzymes the extremely thermophilic archaebacteria may be a possible source. Very stable extracellular enzymes from archaebacteria have also been reported, for reference see J. M. Bragger et al. "Very stable enzymes from extremely thermophilic archaebacteria and eubacteria" in *Appl. Microbiol. Biotechnol.* 31, 1989, p. 556–561. The genus Pyrodictium, however, has not been reported before to produce extracellular amylases, pullulanases and xylanases, in fact it is the first time a member of the family Desulfurococcaceae has been reported to produce an extracellular xylanase. A survey of the taxonomy of the family Desulfurococcaceae is described in "The Prokaryotes; A Handbook on the Biology of Bacteria: Ecophysiology, Isolation, Identification, Applications", 2 nd Ed., Springer-Verlag, Vol I, p. 678.

According to the invention, xylanase is derived from a xylanase producing strain of the family Desulfurococcaceae, in particular the genus Pyrodictium, e.g. *P. abyssi*, and an amylase is derived from an amylase producing strain of the genus Pyrodictium, in particular *P. abyssi*, and a pullulanase is derived from a pullulanase producing strain of the genus Pyrodictium, in particular *P.abyssi*.

A strain representative of *Pyrodictium abyssi* has been made publicly available under Accession No. DSM 6158. The number is published in the DSM Catalogue of Strains, 1993.

Production of Xylanase, Amylase and Pullulanase

Xylanase, amylase and pullulanase of the invention may be produced by anaerobic cultivation of the above mentioned strain on a nutrient medium containing suitable carbon and nitrogen sources, such media being known in the art. Anaerobic conditions may be achieved during the preparation of media by sparging with $H_2/CO_2$ (2 bar overpressure) and following the anaerobic techniques as described by Balch and Wolfe in *Appl. Env. Microbiol.* 32, 1976, pp. 781–791.

Alternatively, xylanase, amylase and pullulanase of the invention can be produced by aerobic cultivation of a transformed host organism containing the appropriate genetic information from the above mentioned strain. Such transformants can be prepared and cultivated by methods known in the art.

The xylanase, amylase and pullulanase may be recovered by removing the cells from the fermentation medium (e.g. by centrifugation or filtration) and then concentrating the broth (e.g. by ultrafiltration). If desired, the xylanase, amylase and pullulanase may be further purified by known methods.

Immunochemical Properties

The enzymes of the invention have immunochemical properties identical or partially identical (i.e. at least partially identical) to those of an enzyme derived from the strain *Pyrodictium abyssi*, DSM 6158.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), chapters 5 and 14. The terms "antigenic identity" and "partial antigenic identity" are described in the same book, Chapters 5, 19 and 20.

Monospecific antisera are generated according to the above mentioned method by immunizing rabbits with the purified enzymes of the invention. The immunogens are mixed with Freund's adjuvant and injected subcutaneously into rabbits every second week. Antisera are obtained after a total immunization period of 8 weeks, and immunoglobulins are prepared therefrom as described by Axelsen N. H., supra.

The Enzymes

A xylanase of the invention can be characterized by having xylanase activity at temperatures of from below 70° C. to approximately 120° C., having activity optimum at temperatures in the range 105–115° C., determined at pH 5.5 with xylan as substrate. The xylanase can also be characterized by having xylanase activity at pH values of from below pH 4.0 to approximately pH 8.5, having optimum in the range pH 5.5 to pH 6.5, determined at 100° C. with xylan as substrate.

An amylase of the invention can be characterized by having amylase activity at temperatures of from below 60° C. to above 120° C., having activity optimum at temperatures in the range 110–120° C., determined at pH 5.5 with starch as substrate.

A pullulanase of the invention can be characterized by having pullulanase activity at temperatures of from below 60° C. to above 120° C., having activity optimum at temperatures in the range 110–120° C., determined at pH 5.5 with pullulan as substrate.

Determination of Amylase Activity

Amylase activity is determined by measuring the amount of reducing sugar released during the incubation with starch. One unit (U) of amylase activity is defined as the amount of amylase that releases 1 μmole of reducing sugar (as maltose standard) per min. under the following assay conditions: A 0.05 ml volume of 1% soluble starch is added to 0.05 ml of 0.1 M sodium acetate buffer pH 5.5. 25 μl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Determination of Pullulanase Activity

Pullulanase activity is determined by measuring the amount of reducing sugar released during the incubation with pullulan. One unit (U) of pullulanase activity is defined as the amount of pullulanase that releases 1 μmole of reducing sugar (as maltose standard) per min. under the following assay conditions: A 0.05 ml volume of 1% pullulan is added to 0.05 ml of 0.1 M sodium acetate buffer pH 5.5. 25 μl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Determination of Xylanase Activity

Xylanase activity is determined by measuring the amount of reducing sugar released during the incubation with xylan. One unit (U) of xylanase activity is defined as the amount of xylanase that releases 1 μmole of reducing sugar (as xylose standard) per min. under the following assay conditions: A 0.05 ml volume of 1% soluble xylan is added to 0.05 ml of 0.1 M sodium acetate buffer pH 5.5. 25 μl of enzyme solution are added to this mixture and the sample is incubated at 90° C. for 30 min. The reaction is stopped by cooling on ice, and the amount of reducing sugar is determined by dinitrosalicylic acid. Sample blanks are used to correct for nonenzymatic release of reducing sugar.

Industrial Applications

The enzymes of this invention possess valuable properties allowing for various industrial applications. In particular the amylase and pullulanase, in being thermostable, find potential application in the production of sweeteners and ethanol from starch. Conditions for conventional starch converting processes and liquefaction and/or saccharification processes are described in for instance U.S. Pat. No. 3,912,590 and EP patent publications Nos. 252,730 and 63,909.

Due to the excellent temperature stability of the xylanase, the xylanase of the invention finds potential application in the paper and pulp industry. Use of xylanase in the paper and pulp industry is disclosed in e.g. WO 93/19171.

The following example further illustrates the present invention, and it is not intended to be in any way limiting to the scope of the invention as claimed.

EXAMPLE 1

Xylanase, Amylase and Pullulanase

The strain *Pyrodictium abyssi*, DSM 6158, was recultured from glycerol-preserved cells using the medium recommended by the Deutsche Sammlung von Mikroorganismen (DSM). The microorganisms were grown in 1 liter of batch cultures under the following conditions: Medium: DSM283 without citric acid (DSM283 is described in DSM Catalogue of Strains, 1993), plus 0.5 g/l of yeast extract plus 0.1 mg/l of $Na_2WO_4X2H_2O$ plus 0.5% (w/v) starch (amylase, pullulanase) or 0.5% (w/v) xylan (xylanase); pH 5.5–6.0; temp. 97° C. The cell density achieved in this medium was $\geq 10^7$ cells/ml. Anaerobic conditions were achieved during the preparation of media by sparging with $H_2/CO_2$ (2 bar overpressure) and following the techniques as described by Balch in *Appl. Env. Microbiol.* 32, 1976, pp. 781–791.

After cultivation the culture fluid was centrifuged at 12.000×g for 30 min. at 4° C., and the cell free supernatant was concentrated up to 100-fold using an Amicon Ultrafiltration System.

The following total activity (U) in supernatant was found:

Amylase activity: 2.2 U/l
Pullulanase activity: 3.0 U/l
Xylanase: 1.5 U/l

Temperature Optima

Temperature optima were determined by incubation of samples for 30 minutes at pH 5.5 at temperatures from 60° C. to 120° C. The incubation was conducted in closed Hungate tubes in order to prevent boiling of the solution.

FIG. 1 (Amylase (♦) and pullulanase (□)) and FIG. 2a (xylanase) show the result.

pH Optima

To determine pH optima of the xylanase, Universal buffer (Britten and Robinson) was used to obtain values from pH 4.0 to pH 8.5. Samples were incubated for 30 minutes at 100° C. at the pH in question.

Figure 2:
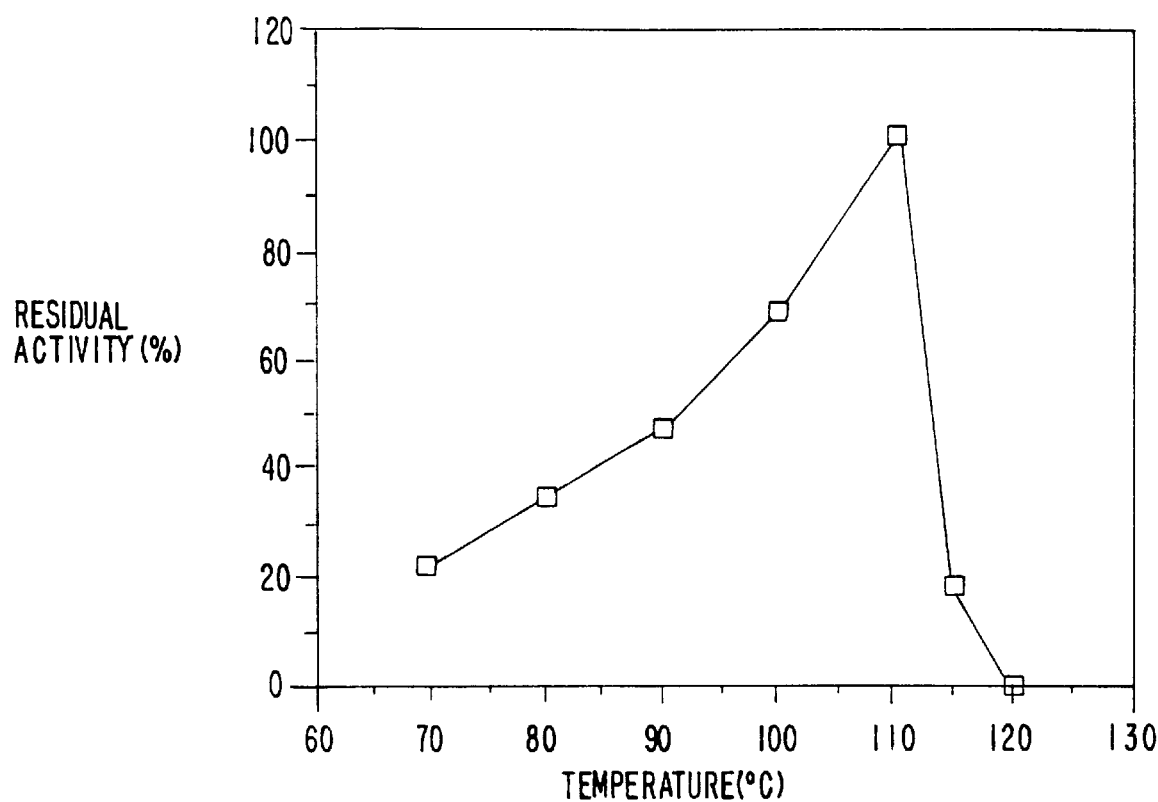
FIG. 2a shows the relative activity (% rel.) of a xylanase of the invention at various temperatures (determined at pH 5.5 with xylan as substrate)
FIG. 2b shows the relative activity of a xylanase of the invention at various pH (determined at 100° C. with xylan as substrate).
Figure 3:
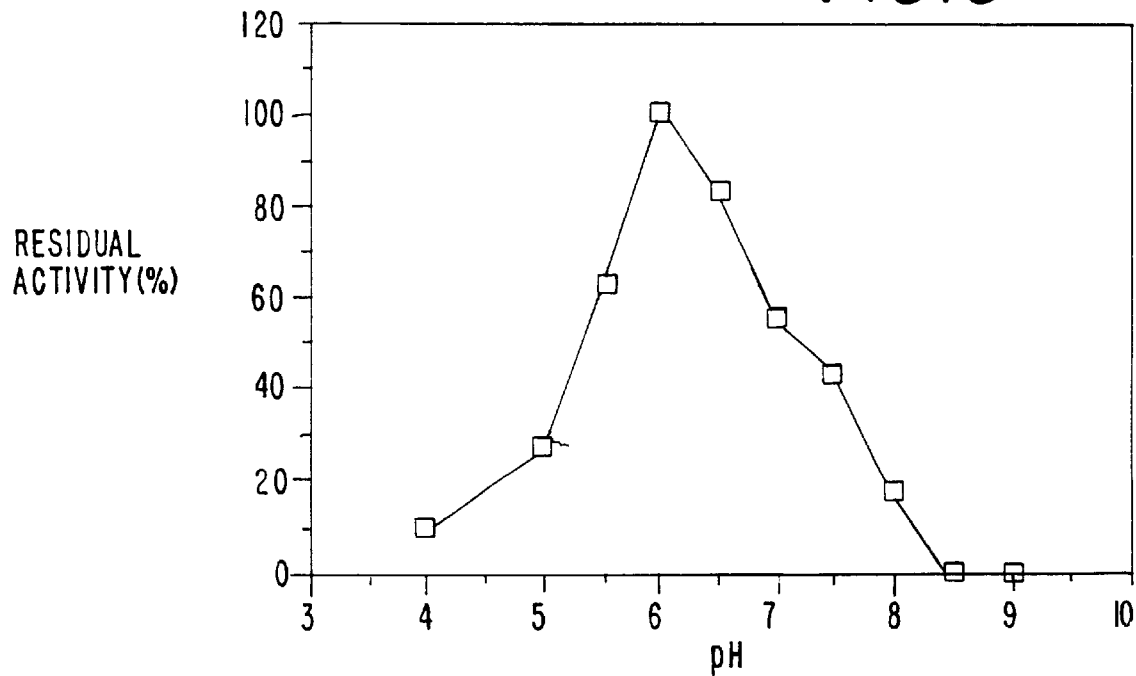

FIG. 2.*b* shows the result.

We claim:

1. An amylase preparation, which is obtained from an amylase producing strain of the genus Pyrodictium, and has activity optimum at temperatures in the range 110–120° C. determined at pH 5.5 with starch as substrate.

2. An amylase preparation according to claim 1, wherein the amylase producing strain belongs to *Pyrodictium abyssi*.

3. An amylase preparation according to claim 2, wherein the amylase producing strain is *Pyrodictium abyssi*, DSM 6158.

4. A method of producing sweeteners from starch comprising incubation of starch with the amylase of claim 1.

5. A method of producing ethanol from starch comprising incubation of starch with the amylase of claim 1.

* * * * *